(12) United States Patent
Paz Rojas et al.

(10) Patent No.: US 9,499,584 B2
(45) Date of Patent: Nov. 22, 2016

(54) GPCR WITH IMPROVED CELL SURFACE EXPRESSION

(75) Inventors: Elier Paz Rojas, Córdoba (ES); Fé Isabel García Maceira, Córdoba (ES); Verónica Inmaculada Luna Guerrero, Córdoba (ES); Maria Gracia Montero Peñalvo, Córdoba (ES); Tania García Maceira, Córdoba (ES); José Andrés Morales Martínez, Córdoba (ES); Ana Belén Aragón Gómez, Córdoba (ES); Ana Quesada Molina, Córdoba (ES); Aurora María Márquez Morales, Córdoba (ES)

(73) Assignee: CANVAX BIOTECH S.L, Córdoba (ES)

(*) Notice: Subject to any disclaimer, the term of this patent is extended or adjusted under 35 U.S.C. 154(b) by 0 days.

(21) Appl. No.: 14/375,316

(22) PCT Filed: Jan. 31, 2012

(86) PCT No.: PCT/EP2012/051532
§ 371 (c)(1),
(2), (4) Date: Dec. 30, 2014

(87) PCT Pub. No.: WO2013/113370
PCT Pub. Date: Aug. 8, 2013

(65) Prior Publication Data
US 2015/0175661 A1    Jun. 25, 2015

(51) Int. Cl.
*C07K 7/08* (2006.01)
*C07K 14/72* (2006.01)
*G01N 33/74* (2006.01)
*G01N 33/68* (2006.01)

(52) U.S. Cl.
CPC ............ *C07K 7/08* (2013.01); *C07K 14/723* (2013.01); *G01N 33/68* (2013.01); *G01N 33/74* (2013.01); *C07K 2319/035* (2013.01); *C12N 2710/16022* (2013.01); *C12N 2710/16222* (2013.01); *G01N 2333/726* (2013.01); *G01N 2500/00* (2013.01); *G01N 2500/10* (2013.01)

(58) Field of Classification Search
None
See application file for complete search history.

(56) References Cited

U.S. PATENT DOCUMENTS

| | | |
|---|---|---|
| 2005/0202403 A1 | 9/2005 | Fowlkes et al. |
| 2010/0120089 A1 | 5/2010 | Choi et al. |

FOREIGN PATENT DOCUMENTS

| | | |
|---|---|---|
| WO | 2006007857 A1 | 1/2006 |
| WO | 2008048037 A1 | 4/2008 |
| WO | 2012013204 A1 | 2/2012 |

OTHER PUBLICATIONS

International Search Report, Nov. 20, 2012.

*Primary Examiner* — Ruixiang Li
(74) *Attorney, Agent, or Firm* — Tristan A. Fuierer; Moore & Van Allen, PLLC

(57) ABSTRACT

The present invention surprisingly shows that the addition of a heterologous viral-GPCR (G protein-coupled receptor) derived sequence at the amino terminal end of GPCRs improves cell surface expression of such receptors in eukaryotic cells. Transfected cells expressing the above heterologous viral GPCRs on their surface are useful for cell based assays to identify test compounds that increases or modulate activity of a GPCR or a ligand of a GPCR for example for drug discovery, development of novel flavors in the food industry or development of sensors based on odor GPCRs. In addition, membrane extracts derived from transfected cells may be used for example for assays of compounds in drug discovery or for development of sensors comprising such membrane extracts for identification and/or quantification of volatile organic compounds.

6 Claims, 1 Drawing Sheet

SEQUENCE LISTING

```
<160> NUMBER OF SEQ ID NOS: 12

<210> SEQ ID NO 1
<211> LENGTH: 105
<212> TYPE: DNA
<213> ORGANISM: Artificial Sequence
<220> FEATURE:
<223> OTHER INFORMATION: Synthetic Construct

<400> SEQUENCE: 1
ctgagcacaa tggccccagg ctccaccgtg ggaacactcg atgccaacat gaccagcgtg      60
aatgccacag aggacgcctg caccaagagc tacagcgcct cctc                     105

<210> SEQ ID NO 2
<211> LENGTH: 36
<212> TYPE: DNA
<213> ORGANISM: Artificial Sequence
<220> FEATURE:
<223> OTHER INFORMATION: Synthetic Construct

<400> SEQUENCE: 2
ctgagcacaa tggccccagg ctccaccgtg ggaaca                               36

<210> SEQ ID NO 3
<211> LENGTH: 1205
<212> TYPE: DNA
<213> ORGANISM: Artificial Sequence
<220> FEATURE:
<223> OTHER INFORMATION: Synthetic Construct

<400> SEQUENCE: 3
ttgctgactt gcgtgaggct ccggtgcccg tcagtgggca gagcgcacat cgcccacagt      60
ccccgagaag ttggggggag gggtcggcaa ttgaaccggt gcctagagaa ggtggcgcgg     120
ggtaaactgg gaaagtgatg tcgtgtactg gctccgcctt tttcccgagg gtgggggaga     180
accgtatata agtgcagtag tcgccgtgaa cgttcttttt cgcaacgggt ttgccgccag     240
aacacaggta agtgccgtgt gtggttcccg cgggcctggc ctctttacgg gttatggccc     300
ttgcgtgcct tgaattactt ccacgcccct ggctgcagta cgtgattctt gatcccgagc     360
ttcgggttgg aagtgggtgg gagagttcga ggccttgcgc ttaaggagcc ccttcgcctc     420
```

| | |
|---|---:|
| gtgcttgagt tgaggcctgg ccctgggcgct ggggccgccg cgtgcgaatc tggtggcacc | 480 |
| ttcgcgcctg tctcgctgct ttcgataagt ctctagccat ttaaaatttt tgatgacctg | 540 |
| ctgcgacgct tttttctgg caagatagtc ttgtaaatgc gggccaagat ctgcacactg | 600 |
| gtatttcggt ttttgggcc gcgggcggcg acggggcccg tgcgtcccag cgcacatgtt | 660 |
| cggcgaggcg gggcctgcga gcgcggccac cgagaatcgg acggggtag tctcaagctg | 720 |
| gccggcctgc tctggtgcct ggcctcgcgc cgccgtgtat cgccccgccc tgggcggcaa | 780 |
| ggctggcccg gtcggcacca gttgcgtgag cggaaagatg gccgcttccc ggccctgctg | 840 |
| cagggagctc aaaatggagg acgcggcgct cgggagagcg ggcgggtgag tcacccacac | 900 |
| aaaggaaaag ggcctttccg tcctcagccg tcgcttcatg tgactccacg gagtaccggg | 960 |
| cgccgtccag gcacctcgat tagttctcga gcttttggag tacgtcgtct ttaggttggg | 1020 |
| gggagggtt ttatgcgatg gagtttcccc acactgagtg ggtggagact gaagttaggc | 1080 |
| cagcttggca cttgatgtaa ttctccttgg aatttgccct ttttgagttt ggatcttggt | 1140 |
| tcattctcaa gcctcagaca gtggttcaaa gtttttttct tccatttcag gtgtcgtgct | 1200 |
| agctt | 1205 |

<210> SEQ ID NO 4
<211> LENGTH: 790
<212> TYPE: DNA
<213> ORGANISM: Artificial Sequence
<220> FEATURE:
<223> OTHER INFORMATION: Synthetic Construct

<400> SEQUENCE: 4

| | |
|---|---:|
| agatctcccg atcccctatg gtgcactctc agtacaatct gctctgatgc cgcatagtta | 60 |
| agccagtatc tgctccctgc ttgtgtgttg gaggtcgctg agtagtgcgc gagcaaaatt | 120 |
| taagctacaa caaggcaagg cttgaccgac aattgcatga agaatctgct tagggttagg | 180 |
| cgttttgcgc tgcttcgcga tgtacgggcc agatatacgc gttgacattg attattgact | 240 |
| agagtcatac ctgtttggat ccaaccgggt aggggaggcg cttttcccaa ggcagtctgg | 300 |
| agcatgcgct ttagcagccc cgctgggcac ttggcgctac acaagtggcc tctggcctcg | 360 |
| cacacattcc acatccaccg gtaggcgcca accggctccg ttctttggtg gcccccttcgc | 420 |
| gccaccttct actcctcccc tagtcaggaa gttcccccccc gccccgcagc tcgcgtcgtg | 480 |
| caggacgtga caaatggaag tagcacgtct cactagtctc gtgcagatgg acagcaccgc | 540 |
| tgagcaatgg aagcgggtag gccttttggg cagcggccaa tagcagcttt gctccttcgc | 600 |
| tttctgggct cagaggctgg gaaggggtgg gtccgggggc gggctcaggg gcgggctcag | 660 |
| gggcggggcg ggcgcccgaa ggtcctccgg aggcccggca ttctgcacgc ttcaaaagcg | 720 |
| cacgtctgcc gcgctgtcct cctcttcctc atctcgggct cgagtaggaa ttatctgcgg | 780 |
| cctagctagc | 790 |

<210> SEQ ID NO 5
<211> LENGTH: 428
<212> TYPE: DNA
<213> ORGANISM: Artificial Sequence
<220> FEATURE:
<223> OTHER INFORMATION: Synthetic Construct

<400> SEQUENCE: 5

| | |
|---|---:|
| cgacctcatg gctgcgcccc gacacccgcc aacacccgct gacgcctgac gggcttgtct | 60 |

```
gctcccggca tccgcttaca gacaagctgt gaccgtctcc gggagctgca tgtgtcagag    120
gttttcaccg tcatcaccga aacgcgcgag gcagccggat cataatcagc cataccacat    180
ttgtagaggt tttacttgct ttaaaaaacc tcccacacct cccctgaac ctgaaacata     240 aaatgaatgc aattgttgtt gttaacttgt ttattgcagc ttataatggt tacaaataaa    300
gcaatagcat cacaaatttc acaaataaag cattttttc actgcattct agttgtggtt     360
tgtccaaact catcaatgta tcttatcatg tctggatccg ccttgccgg cctcgagcgg     420 ccgctagc                                                             428
```

<210> SEQ ID NO 6
<211> LENGTH: 479
<212> TYPE: DNA
<213> ORGANISM: Artificial Sequence
<220> FEATURE:
<223> OTHER INFORMATION: Synthetic Construct

<400> SEQUENCE: 6

```
agtctccaga aaagggggg aatgaaagac cccacctgta ggtttggcaa gctagcttaa     60
gtaacgccat tttgcaaggc atggaaaat acataactga gaatagagaa gttcagatca    120
aggtcaggaa cagatggaac agctgaatat gggccaaaca ggatatctgt ggtaagcagt    180
tcctgccccg gctcagggcc aagaacagat ggaacagctg aatatgggcc aaacaggata    240
tctgtggtaa gcagttcctg ccccggctca gggccaagaa cagatggtcc ccagatgcgg    300
tccagccctc agcagtttct agagaaccat cagatgtttc agggtgccc caaggacctg    360 aaatgaccct gtgccttatt tgaactaacc aatcagttcg cttctcgctt ctgttcgcgc    420
gcttctgctc cccgagctca ataaaagagc ccacaacccc tcactcgggg cgccagtcc    479
```

<210> SEQ ID NO 7
<211> LENGTH: 5348
<212> TYPE: DNA
<213> ORGANISM: Artificial Sequence
<220> FEATURE:
<223> OTHER INFORMATION: Synthetic Construct

<400> SEQUENCE: 7

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgt atatcgaatt cagtctccag aaaaggggg     240 gaatgaaaga ccccacctgt aggtttggca agctagctta agtaacgcca ttttgcaagg    300 catgaaaaa tacataactg agaatagaga agttcagatc aaggtcagga acagatggaa    360
cagctgaata tgggccaaac aggatatctg tggtaagcag ttcctgcccc ggctcagggc    420
caagaacaga tggaacagct gaatatgggc caaacaggat atctgtggta agcagttcct    480
gccccggctc agggccaaga acagatggtc cccagatgcg gtccagccct cagcagtttc    540
tagagaacca tcagatgttt ccagggtgcc caaggacct gaaatgaccc tgtgccttat    600
ttgaactaac caatcagttc gcttctcgct tctgttcgcg cgcttctgct cccgagctc    660 aataaaagag cccacaacccc tcactcgggg cgccagtcc aagcttggta ccgagctcgg    720
atcgatcatg gagacagaca cactcctgct atgggtactg ctgctctggg ttccaggttc    780
caccggtgac gaacaaaaac tcatctcaga agaggatctg ggccatcgc gactgagcac    840 aatggcccca ggctccaccg tgggaacact cgagggatcc gcggccgctc tagagggccc    900
```

```
tattctatag tgtcacctaa atgctagagc tcgctgatca gcctcgactg tgccttctag    960
ttgccagcca tctgttgttt gccctcccc cgtgccttcc ttgaccctgg aaggtgccac   1020
tcccactgtc ctttcctaat aaaatgagga aattgcatcg cattgtctga gtaggtgtca   1080
ttctattctg gggggtgggg tggggcagga cagcaagggg gaggattggg aagacaatag   1140
caggcatgct ggggatgcgg tgggctctat ggcttctgag gcggaaagaa ccagctgggg   1200
ctctaggggg tatccccacg cgccctgtag cggcgcatta agcgcggcgg gtgtggtggt   1260
tacgcgcagc gtgaccgcta cacttgccag cgccctagcg cccgctcctt tcgctttctt   1320
ccctcctttc ctcgccacgt tcgccggctt tccccgtcaa gctctaaatc gggggctccc   1380
tttagggttc cgatttagtg ctttacggca cctcgacccc aaaaaacttg attagggtga   1440
tggttcacgt agtgggccat cgccctgata gacggttttt cgccctttga cgttggagtc   1500
cacgttcttt aatagtggac tcttgttcca aactggaaca cactcaacc ctatctcggt    1560 ctattctttt gatttataag ggattttgcc gatttcggcc tattggttaa aaatgagct    1620 gatttaacaa aaatttaacg cgaattaatt ctgtggaatg tgtgtcagtt agggtgtgga   1680
aagtccccag gctccccagc aggcagaagt atgcaaagca tgcatctcaa ttagtcagca   1740
accaggtgtg gaaagtcccc aggctcccca gcaggcagaa gtatgcaaag catgcatctc   1800
aattagtcag caaccatagt cccgccccta actccgccca tcccgcccct aactccgccc   1860
agttccgccc attctccgcc ccatggctga ctaatttttt ttatttatgc agaggccgag   1920
gccgcctctg cctctgagct attccagaag tagtgaggag gcttttttgg aggcctaggc   1980
ttttgcaaaa agctcccggg agcttgtata tccattttcg gatctgatca agagacagga   2040
tgaggatcgt ttcgcatgat tgaacaagat ggattgcacg caggttctcc ggccgcttgg   2100
gtggagaggc tattcggcta tgactgggca caacagacaa tcggctgctc tgatgccgcc   2160
gtgttccggc tgtcagcgca ggggcgcccg gttcttttg tcaagaccga cctgtccggt    2220
gccctgaatg aactgcagga cgaggcagcg cggctatcgt ggctggccac gacgggcgtt   2280
ccttgcgcag ctgtgctcga cgttgtcact gaagcgggaa gggactggct gctattgggc   2340
gaagtgccgg ggcaggatct cctgtcatct caccttgctc ctgccgagaa agtatccatc   2400
atggctgatg caatgcggcg gctgcatacg cttgatccgg ctacctgccc attcgaccac   2460
caagcgaaac atcgcatcga gcgagcacgt actcggatgg aagccggtct tgtcgatcag   2520
gatgatctgg acgaagagca tcaggggctc gcgccagccg aactgttcgc caggctcaag   2580
gcgcgcatgc ccgacggcga ggatctcgtc gtgacccatg gcgatgcctg cttgccgaat   2640
atcatggtgg aaaatggccg cttttctgga ttcatcgact gtggccggct gggtgtggcg   2700
gaccgctatc aggacatagc gttggctacc cgtgatattg ctgaagagct tggcggcgaa   2760
tgggctgacc gcttcctcgt gctttacggt atcgccgctc ccgattcgca gcgcatcgcc   2820
ttctatcgcc ttcttgacga gttcttctga gcgggactct ggggttcgaa atgaccgacc   2880
aagcgacgcc caacctgcca tcacgagatt tcgattccac cgccgccttc tatgaaaggt   2940
tgggcttcgg aatcgttttc cgggacgccg gctggatgat cctccagcgc ggggatctca   3000
tgctggagtt cttcgcccac cccaacttgt ttattgcagc ttataatggt tacaaataaa   3060
gcaatagcat cacaaatttc acaaataaag catttttttc actgcattct agttgtggtt   3120
tgtccaaact catcaatgta tcttatcatg tctgtatacc gtcgacctct agctagagct   3180
tggcgtaatc atggtcatag ctgtttcctg tgtgaaattg ttatccgctc acaattccac   3240
```

```
acaacatacg agccggaagc ataaagtgta aagcctgggg tgcctaatga gtgagctaac    3300
tcacattaat tgcgttgcgc tcactgcccg ctttccagtc gggaaacctg tcgtgccagc    3360
tgcattaatg aatcggccaa cgcgcgggga gaggcggttt gcgtattggg cgctcttccg    3420
cttcctcgct cactgactcg ctgcgctcgg tcgttcggct gcggcgagcg gtatcagctc    3480
actcaaaggc ggtaatacgg ttatccacag aatcagggga taacgcagga aagaacatgt    3540
gagcaaaagg ccagcaaaag gccaggaacc gtaaaaaggc cgcgttgctg gcgtttttcc    3600
ataggctccg cccccctgac gagcatcaca aaaatcgacg ctcaagtcag aggtggcgaa    3660
acccgacagg actataaaga taccaggcgt ttccccctgg aagctccctc gtgcgctctc    3720
ctgttccgac cctgccgctt accggatacc tgtccgcctt tctcccttcg ggaagcgtgg    3780
cgctttctca tagctcacgc tgtaggtatc tcagttcggt gtaggtcgtt cgctccaagc    3840
tgggctgtgt gcacgaaccc cccgttcagc ccgaccgctg cgccttatcc ggtaactatc    3900
gtcttgagtc caacccggta agacacgact tatcgccact ggcagcagcc actggtaaca    3960
ggattagcag agcgaggtat gtaggcggtg ctacagagtt cttgaagtgg tggcctaact    4020
acggctacac tagaagaaca gtatttggta tctgcgctct gctgaagcca gttaccttcg    4080
gaaaaagagt tggtagctct tgatccggca aacaaaccac cgctggtagc ggtttttttg    4140
tttgcaagca gcagattacg cgcagaaaaa aaggatctca agaagatcct ttgatctttt    4200
ctacggggtc tgacgctcag tggaacgaaa actcacgtta agggattttg gtcatgagat    4260
tatcaaaaag gatcttcacc tagatccttt taaattaaaa atgaagtttt aaatcaatct    4320
aaagtatata tgagtaaact tggtctgaca gttaccaatg cttaatcagt gaggcaccta    4380
tctcagcgat ctgtctattt cgttcatcca tagttgcctg actccccgtc gtgtagataa    4440
ctacgatacg ggagggctta ccatctggcc ccagtgctgc aatgataccg cgagacccac    4500
gctcaccggc tccagattta tcagcaataa accagccagc cggaagggcc gagcgcagaa    4560
gtggtcctgc aactttatcc gcctccatcc agtctattaa ttgttgccgg gaagctagag    4620
taagtagttc gccagttaat agtttgcgca acgttgttgc cattgctaca ggcatcgtgg    4680
tgtcacgctc gtcgtttggt atggcttcat tcagctccgg ttcccaacga tcaaggcgag    4740
ttacatgatc ccccatgttg tgcaaaaaag cggttagctc cttcggtcct ccgatcgttg    4800
tcagaagtaa gttggccgca gtgttatcac tcatggttat ggcagcactg cataattctc    4860
ttactgtcat gccatccgta agatgctttt ctgtgactgg tgagtactca accaagtcat    4920
tctgagaata gtgtatgcgg cgaccgagtt gctcttgccc ggcgtcaata cgggataata    4980
ccgcgccaca tagcagaact ttaaaagtgc tcatcattgg aaaacgttct tcggggcgaa    5040
aactctcaag gatcttaccg ctgttgagat ccagttcgat gtaacccact cgtgcaccca    5100
actgatcttc agcatctttt actttcacca gcgtttctgg gtgagcaaaa acaggaaggc    5160
aaaatgccgc aaaaaaggga ataagggcga cacggaaatg ttgaatactc atactcttcc    5220
tttttcaata ttattgaagc atttatcagg gttattgtct catgagcgga tacatatttg    5280
aatgtattta gaaaaataaa caataggggg ttccgcgcac atttccccga aaagtgccac    5340
ctgacgtc                                                            5348
```

<210> SEQ ID NO 8
<211> LENGTH: 35
<212> TYPE: PRT
<213> ORGANISM: Artificial Sequence
<220> FEATURE:
<223> OTHER INFORMATION: Synthetic Construct

```
<400> SEQUENCE: 8

Leu Ser Thr Met Ala Pro Gly Ser Thr Val Gly Thr Leu Asp Ala Asn
1               5                   10                  15

Met Thr Ser Val Asn Ala Thr Glu Asp Ala Cys Thr Lys Ser Tyr Ser
            20                  25                  30

Ala Phe Leu
        35

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

Leu Ser Thr Met Ala Pro Gly Ser Thr Val Gly Thr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Glu Gln Lys Leu Ile Ser Glu Glu Asp Leu Asn
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Leu Ala Ala Met Ala Pro Gly Ala Ala Val Gly Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct

<400> SEQUENCE: 12

Leu Ala Ala Met Ala Pro Gly Ala Thr Val Gly Thr
1               5                   10
```

GPCR WITH IMPROVED CELL SURFACE EXPRESSION

CROSS-REFERENCE TO RELATED APPLICATIONS

This application is filed under the provisions of 35 U.S.C. §371 and claims the priority of International Patent Application No. PCT/EP2012/051532 filed on 31 Jan. 2012 entitled "GPCR WITH IMPROVED CELL SURFACE EXPRESSION" in the name of Elier PAZ ROJAS, et al., which is hereby incorporated by reference herein in its entirety.

FIELD OF THE INVENTION

The present invention may be included in the biotechnological and pharmaceutical fields. The present invention shows that the addition of a viral-GPCR (G protein-coupled receptor) derived sequence at the amino terminal end of GPCRs improves cell surface expression of such receptors in eukaryotic cells. This improvement on cell surface expression by such heterologous viral-GPCR derived sequence may be reached in either primary or established cell lines, for example mammalian hematopoietic or non-hematopoietic cell lines and in stably transfected or transiently transfected cells. Such heterologous sequence may be combined with a signal peptide and/or a peptide tag for surface detection and/or separation of GPCR positive cells. In addition useful promoters for expression of a GPCR comprising at least a heterologous viral-GPCR derived sequence may be selected from either non-silenced constitutive promoters or inducible promoters.

Transfected cells expressing the above heterologous viral-GPCRs on their surface are useful for cell based assays to identify test/candidate compounds that increases or modulate activity of a GPCR or a ligand of a GPCR for example for drug discovery, development of novel flavors in the food industry or development of sensors based on odor GPCRs. In addition, membrane extracts derived from transfected cells may be used for example for assays of compounds in drug discovery or for development of sensors comprising such membrane extracts for identification and/or quantification of volatile organic compounds.

STATE OF THE ART

Cell surface receptors for ligands are the molecular entities by which a cell senses its surrounding environment. After a ligand-receptor interaction, the cell directs cellular processes in response to this interaction. GPCRs, also known as seven-transmembrane receptors, comprise the largest family of cell surface receptors yet identified. Over 60% of current prescription drugs are targeted towards GPCRs, and as such, GPCRs are one of the most important targets for drug discovery research. To date, about 400 genes have been identified as GPCRs. But also, GPCRs are the receptors used for sensing odors and tastes.

GPCRs operate through a similar molecular mechanism. Activation of GPCR by extracellular stimuli causes conformational changes in the receptor, which results in the intermediate coupling and activation of GTP-binding proteins (G proteins). G proteins are heterotrimeric in nature and are composed of α, β, and γ subunits encoded by distinct genes. The α subunit is responsible for the binding of GDP and GTP. Binding of a ligand to a GPCR results in a transition of the α subunit from a GDP-bound form to a GTP-bound form and leads to the activation of the heterotrimer through dissociation of the α-GTP from the βγ dimer. Both α-GTP and the βγ dimer regulate the activities of a variety of effectors that transmit the signal to the cell interior through the production of second messenger molecules (e.g., calcium, cAMP, etc). There are at least 17 Ga genes, and members of G proteins can be grouped into four main classes termed $G\alpha i/_0$, $G\alpha_q$, $G\alpha_{15}$ and $G\alpha_{12}$. Upon ligand binding GPCRs can couple to a variety of G proteins, thus leading to activation of many complex signaling pathways, which can complicate the readout for High Throughput Screening (HTS) of GPCRs.

Binding of a ligand to a particular GPCR initiates a signal that is detected by measuring some change in properties of some element of the signaling pathway, mainly second messengers like intracellular calcium, cyclic AMP and inositol phosphate metabolites. A universal read-out for most GPCRs is beneficial for drug discovery for both simplicity and for deorphanization of receptors without known ligands. It is known in the state of the art that certain endogenous promiscuous G-proteins can couple with many GPCRs [Wilkie T M, Scherle P A, Strathman M P, Slepak V Z and Simon M I. *Proc. Natl. Acad. Sci. USA* 88: 10049-10053 (1991)] and [Amatruda T T, Steele D A., Slepak V Z. and Simon M I. *Proc. Natl. Acad. Sci. USA* 88: 5587-5591 (1991)] but such endogenous promiscuous G-proteins are naturally expressed only in certain hematopoietic cells like myelomonocytic cells and T cells in humans and myelomonocytic cells, B cells and certain T cells in mouse and rat. But expression of most GPCRs is difficult to be achieved in most hematopoietic cells.

An alternative is to co-transfect both a GPCR and a promiscuous G-protein coupled receptor into non-hematopoietic cells, but there is also the need to express the GPCR in such cell lines at high level for improved sensitivity. Also some researchers want to use primary cells for screening but those cells express normally low levels of GPCR and thus sensitivity is low. An alternative could be to transfect the target GPCR into such primary cells to improve sensitivity while keeping the cellular background as close as possible to that of target disease. But primary cells are difficult to transfect, they can not be cultivated in vitro for long periods of time and thus they can not be stably transfected. Thus, for both non-hematopoietic cells and primary cells improved methods for GPCR expression are needed.

One common technology to screen GPCR drug targets is measuring the changes in intracellular calcium upon binding of ligands to GPCRs in a high throughput manner. However, not all GPCRs couple to $G\alpha_q$ leading to calcium mobilization.

It is known in the state of the art that hematopoietic cells express endogenous promiscuous G-proteins such as $G\alpha_{15}$ and/or $G\alpha_{16}$ at high levels [Wilkie T M, Scherle P A, Strathman M P, Slepak V Z and Simon M I. *Proc. Natl. Acad. Sci. USA* 88: 10049-10053 (1991)] and [Amatruda T T, Steele D A., Slepak V Z. and Simon M I. *Proc. Natl. Acad. Sci. USA* 88: 5587-5591 (1991)]; the entire teachings of which are incorporated herein by reference. Unfortunately many GPCRs are difficult to be expressed at high levels in the cell surface, particularly in the surface of hematopoietic cells.

One alternative method for coupling a non-$G\alpha_q$ coupled receptor to the calcium pathway is to co-transfect either promiscuous G protein (e.g. $G\alpha_{15}$) or $G\alpha_q$ chimeras to link GPCR activation to calcium mobilization. In this method there is also the need to express GPCRs on the cell surface at adequate levels for screening.

Also sometimes it is desired to use primary cell lines for screening drugs, particularly to use a cell line as close as possible to the cell type of the target disease to which drugs are to be developed. Levels of endogenous GPCRs on the cell surface are low for primary cells and thus only high affinity binders are identified with primary cells. But primary cell lines are difficult to be transfected and they can not be cultivated for long periods of time and thus stable transfection is normally not possible.

GPCRs are also the receptors expressed in the olfactory bulb that mediate odor recognition. Human express about 400 functional GPCRs in their olfactory bulb and rodents express about 1000 functional GPCRs. But expression of GPCRs on the surface of heterologous cells is extremely low. One of the strategies used to improve cell surface expression of olfactory GPCRs on the surface of heterologous cells is the use of chaperones like RTP1S and REEP alone or in conjunction with N-terminal sequences derived from rhodopsin receptor. Novel sequences that improve cell surface expression are needed.

It is well known in the state of the art that glycosylation is a common post-translational modification of seven transmembrane spanning G-protein-coupled receptors (GPCR). Two common forms of glycosylation are known in the state of the art: N-linked glycosylation and O-linked glycosylation. N-linked glycosylation is the process of modification by oligosaccharides of asparagine or arginine side chains and is important for the folding of some eukaryotic proteins. N-linked glycosylation occurs normally in eukaryotes in the lumen of the endoplasmic reticulum. O-linked glycosylation involves the glycan linking to the hydroxyl side chain of serine or threonine via an N-acetylgalactosamine. O-linked glycosylation occurs in the Golgi apparatus.

Although glycosylation has been shown to be important for protein folding, trafficking and targeting of the receptors to the cell surface, examples of glycosylation that are relevant for surface expression of GPCRs are limited to N-linked glycosylation. In fact, there is no prior art regarding O-linked glycosylation in GPCRs. As a consequence, at present, it is not known whether O-linked glycosylation improves surface expression of GPCRs or whether the addition of a heterologous sequence at the amino terminal of GPCRs produces O-linked glycosylation and the effect of such potential glycosylation for the surface expression of GPCRs.

The synthesis and intracellular sorting of the interleukin-2 (IL-2) receptor has been studied in a line of mutant Chinese hamster ovary (CHO) cells with a reversible defect in protein O-glycosylation (Kozarsky, K F et al, Mol. Cell. Biol. 1988, 8(8), 3357). Carbohydrate deficient IL-2 receptors were missorted and resulted in very little surface expression. Several other receptors are known in the state of the art to be linked to O-glycosylation for their improved surface expression or their increased stability to proteolysis. Examples of such receptors are the low-density lipoprotein receptor, decay-accelerating factor, and the major antigen envelope protein of Epstein-Barr virus. But for others secreted proteins and receptors such as human chorionic gonadotropin (Matzuk et al. 1987); Apoprotein E (Zanni et al (1989); gp120/41 envelope protein of HIV there is no effect of O-linked glycosylation in their expression levels or stability. But again, the above examples do not teach us if O-linked glycosylation exist in GPCRs and the effect of such potential O-glycosylation on the surface expression levels of GPCRs. Moreover, the above examples using native receptors not related to GPCR do not demonstrate or anticipate that the addition of such sequences to heterologous GPCRs improve their surface expression.

In the present invention it is described that certain viral derived GPCR sequences when added to the amino terminal end of heterologous GPCRs improve their surface expression. It is also demonstrated that mutations of serine and threonines present on such viral derived GPCR sequences reduces partially but not all the cell surface expression improvement reached by including such viral sequences. In addition we demonstrate that such improvement in surface expression of GPCRs is reached in both cells of hematopoietic and non-hematopoietic origin. Such cells expressing this modified receptor may be used for cell based assays for example for drug discovery, or membranes derived from such cells should be used in assays where GPCRs are needed.

DESCRIPTION OF THE INVENTION

As cited above, the present invention surprisingly shows that the addition of a viral-GPCR derived sequence at the amino terminal end of GPCRs improves cell surface expression of such receptors. This improvement on cell surface expression by a viral-GPCR derived sequence may be reached in eukaryotic cells for example, mammalian primary or established cell lines such as hematopoietic or non-hematopoietic cell lines.

In one particular embodiment of the present invention the viral-GPCR derived sequence is SEQ ID NO: 1. In a preferred embodiment the viral-GPCR derived sequence is a shorter form of SEQ ID NO: 1 designed as SEQ ID NO: 2. In another embodiment the above sequences may be present once or in tandem of two or more sequences. In a preferred embodiment the SEQ ID NO: 1 encodes for the SEQ ID NO: 8 and the SEQ ID NO: 2 encodes for the SEQ ID NO: 9.

The viral sequences added at the amino terminal end of GPCRs are made as DNA chimeric molecules where the viral sequences are added for example between a sequence coding for a peptide tag and the second amino acid coding for a mature GPCR. Such viral sequences added at the amino terminal end of GPCRs are preferably isolated from BILF1 open reading frame from Epstein-Barr virus. Such sequences when added to the amino terminal of heterologous GPCRs improve their surface expression by either improving the percentage of positive cells or improving the mean or the median of the number of GPCRs molecules on the surface of each cell. However, the viral-GPCR sequences of the invention may derive from others beta- and gamma-herpesviruses, for example from all members of the beta-herpesvirus family, e.g., cytomegalovirus (CMV), encode GPCR homologs and gamma2-herpesviruses, e.g., Kaposi's sarcoma-associated herpesvirus (KSHV) and gamma1-herpesviruses, e.g., Epstein-Barr virus also encode GPCR homologs. In certain embodiments of the present invention the viral-GPCR derived sequence used to improve the surface expression of GPCRs is selected from the first 30 amino acids of a group of viral GPCR comprising UL33, M33, R33, UL78, M78, R78, US27, and US28.

In another preferred embodiment, the vectors comprising the viral GPCR derived sequence of the invention also comprise a signal peptide to further improve surface expression (overexpression) or a sequence tag for surface detection and/or separation of GPCR positive cells for example by flow cytometry or by magnetic beads.

In another embodiment of the present invention the viral-GPCR derived sequence is stably transfected in a cell line.

In preferred embodiment, the viral-GPCR derived sequence of the invention is transiently transfected in a eukaryotic cell line or in a eukaryotic primary cell. In a further embodiment of the present invention cell lines or primary cells transiently or stably transfected with the GPCR are sorted for physical separation of GPCR positive cells. In one embodiment the cell transfected with a GPCR comprising at least a heterologous viral-GPCR derived sequence is an eukaryotic cell. In one specific embodiment the cell transfected with a GPCR comprising at least a heterologous viral-GPCR derived sequence is a mammalian hematopoietic cell or a mammalian non-hematopoietic cell.

In one embodiment of the present invention the GPCR comprising at least a heterologous viral-GPCR derived sequence is expressed under the control of a constitutive promoter. In a further embodiment the promoters are selected from non-silenced promoters for the specific cell line to be transfected. In a still further embodiment the non-silenced promoters are selected from either ubiquitous or viral promoters. In one embodiment suitable promoters for constitutive GPCR expression may be selected from a group comprising human or mouse elongation factor 1-alpha promoters (SEQ ID NO: 3), phosphoglycerate kinase promoters (SEQ ID NO: 4) from human, mouse and rat species, Rous Sarcoma Virus (RSV) promoter (SEQ ID NO: 5), 5'LTR from Moloney Murine Leukaemia Virus promoter MoMLV-5'LTR (SEQ ID NO: 6) and Ubiquitin promoter from either human, mouse and rat species. Such promoters are not silenced over time when hematopoietic cells are used in the methods of the present invention and are also suitable when non-hematopoietic cells are used in the methods of the present invention. In another embodiment of the present invention suitable promoters for surface expression of GPCR are inducible promoters.

In one embodiment of the present invention the GPCR comprising at least a heterologous viral-GPCR derived sequence is expressed under the control of an inducible promoter. In a particular embodiment suitable inducible promoters are selected from a group comprising tetracycline inducible promoter, ecdysone inducible promoter, cumate inducible promoter and progesterone inducible promoter.

As described above, exogenous nucleic acid sequences that encode one or more GPCRs with at least a heterologous viral-GPCR derived sequence at the amino terminal region are introduced into eukaryotic cells. As used herein, an exogenous nucleic acid sequence refers to a nucleic acid sequence that does not naturally occur in the cell and/or has been introduced into a cell (e.g., a host cell, a progenitor (ancestor) cell). Any nucleic acid sequence (e.g., DNA, RNA) that can encode a GPCR with at least a heterologous viral-GPCR derived sequence such as SEQ ID NO: 1 or SEQ ID NO: 2 at the amino terminal region and that is exogenously expressed can be used in the present invention.

Introduction of exogenous nucleic acid sequences is well known in the art, and can be performed, for example, through transfection. In one embodiment, an exogenous nucleic acid sequence that encodes a GPCR with at least a heterologous viral-GPCR derived sequence at the amino terminal region is introduced into a cell as a plasmid or vector. In one embodiment of the present invention transfection may be either transient or stable transfection.

In one embodiment, the invention refers to plasmid or vector comprising a nucleic acid sequence encoding a GPCR with at least a heterologous viral-GPCR derived sequence such as SEQ ID NO: 1 or SEQ ID NO: 2 at the amino terminal region, wherein the GPCR is expressed at a high level. In another embodiment, the plasmid comprises a nucleic acid sequence encoding a G-protein coupled receptor (GPCR) with at least a heterologous viral-GPCR derived sequence such as SEQ ID NO: 1 or SEQ ID NO: 2 at the amino terminal region, wherein the nucleic acid sequence encoding the GPCR further comprises a promoter that is operably linked to the GPCR.

In one particular embodiment a vector useful for constitutive GPCR expression is P-MoMLV-5'LTR-SP-cmyc-tag-VGS-MCS-polyA (SEQ ID NO: 7) that comprises a strong constitutive promoter that is not silenced in either hematopoietic cells or non-hematopoietic cells, a signal peptide to aid in translocation across the membrane, a tag for selection of cells with the GPCR on surface, a heterologous viral-GPCR derived sequence to improve membrane expression and a polyadenylation sequence to stabilize messenger RNA. If the sequence of the P-MoMLV5'LTR promoter in the vector of sequence SEQ ID NO: 7 is replaced by tetracycline inducible promoter then a vector suitable for inducible GPCR expression is obtained. The present invention is the first to demonstrate that the addition of SEQ ID NO: 1 or SEQ ID NO: 2, a heterologous viral-GPCR derived sequence, at the N-terminal end of a GPCR improves cell surface receptor expression in eukaryotic cells and that this improvement is not restricted to mammalian hematopoietic cells as previously discovered by us.

Cells with improved surface expression of GPCRs of the present invention are in general useful for testing interactions between at least two molecules, at least one acting as ligand or agonist and at least a GPCR. For example, in drug discovery thousands or even millions of small molecules are tested against a target to find small molecules that modify the activity of such target. In a particular example, compounds are screened for agonists or antagonist of G-protein coupled receptors, a highly druggable class of receptors. Such interactions may be tested using either cell based assays or membrane enriched fractions of cells with improved surface GPCR expression. Examples of cell based assays are: label-free assays, second messengers dependent assays that measure levels of for example intracellular calcium, cyclic AMP and inositol phosphate metabolites. Examples of uses of membrane fractions of GPCR positive cells are affinity based screening technologies such as radioligand binding assays and surface plasmon resonance sensors coated with membrane fractions from cells expressing GPCRs on their surface. In addition, sensors based on GPCRs with viral GPCR derived sequences can be used for diagnostic, in particular sensors for volatile organic compounds detection. Plasmids with viral GPCR derived sequences may be used for the development of cell lines with improved expression of GPCRs either as transient or stable cell populations to be used in cell based assays or for production of membrane fractions enriched in GPCRs.

Therefore, the present invention also comprises methods and kits for testing if a compound interacts with a GPCR and/or to quantitate interaction between a GPCR and a compound. Such kit comprises at least: a cell line or a membrane enriched fraction of a cell line comprising a G-protein coupled receptor with at least a heterologous viral-GPCR derived sequence at the amino terminal end under the control of a suitable promoter. Such cell line may also express either an endogenous or a transfected promiscuous G-protein. For cell based assays the above kit should comprise also a substrate for determination of GPCR activity (e.g. a fluorescent substrate for measuring intracellular calcium rise or a substrate of aequorin or a substrate for measuring cell regulated exocytosis).

The improvements of cell surface expression reached in the present invention offer the possibility of preparing GPCR enriched membranes for example for radioligand binding assays or for functional assays with live cells such as label-free assays, second messenger assays like intracellular calcium mobilization, cAMP increase, inositol phosphates production or release of granule stored enzymes in hematopoietic cells with professional regulated exocytosis.

The following terms are defined only for the purpose of the present invention:

Surface receptor: It refers to molecules that occur on the surface of cells, interact with the extracellular environment and transmit or transduce the information regarding the environment intracellularly in a manner that ultimately modulates transcription of specific promoters, resulting in transcription of specific genes. Examples of surface receptor are tyrosine kinase receptors, ion channel receptors, cytokine receptors, G-protein coupled receptors (GPCRs) such as chemoattractant peptide receptors, neuropeptide receptors, light receptors, neurotransmitter receptors, polypeptide hormone receptors or odorant receptors.

G protein-coupled receptors (GPCRs), also known as seven transmembrane receptors, 7TM receptors, heptahelical receptors, and G protein linked receptors (GPLR): They are a large protein family of transmembrane receptors characterized by seven membrane-spanning domains with an extracellular N terminus and a cytoplasmic C terminus. Ligand binding to GPCRs promotes conformational changes leading to small G-protein coupling, the initiation of signal transduction pathways, and ultimately to cellular responses. The ligands that bind and activate these receptors include light-sensitive compounds, odors, pheromones, hormones, and neurotransmitters, and vary in size from small molecules to peptides to large proteins. G protein-coupled receptors are only found in higher eukaryotes, including yeast, plants, and, especially, animals. G protein-coupled receptors are involved in many diseases, but are also the target of around half of all modern medicinal drugs. GPCRs operate through a similar molecular mechanism. Activation of GPCR by extracellular stimuli causes conformational changes in the receptor, which results in the intermediate coupling and activation of GTP-binding proteins (G proteins). G proteins are heterotrimeric in nature and are composed of $\alpha$, $\beta$, and $\gamma$ subunits encoded by distinct genes. The $\alpha$ subunit is responsible for the binding of GDP and GTP. Binding of a ligand to a GPCR results in a transition of the $\alpha$ subunit from a GDP-bound form to a GTP-bound form and leads to the activation of the heterotrimer through dissociation of the $\alpha$-GTP from the $\beta\gamma$ dimer. Both $\alpha$-GTP and the $\beta\gamma$ dimer regulate the activities of a variety of effectors that transmit the signal to the cell interior through the production of second messenger molecules (e.g., calcium, cAMP, etc). There are at least 17 Ga genes, and members of G proteins can be grouped into four main classes termed $G\alpha i/_o$, $G\alpha_q$, $G\alpha_{15}$ and $G\alpha_{12}$. Upon ligand binding GPCRs can couple to a variety of G proteins, thus leading to activation of many complex signaling pathways, which can complicate the readout for High Throughput Screening (HTS) of GPCRs.

"Heterologous viral-GPCR derived sequence" or a "viral-GPCR derived sequence": For the purpose of the present invention, it refers to any sequence derived from non-eukaryotic organisms, mainly viruses, said sequence being transferred into eukaryotic cells, acting as recipients, preferably by means of expression vectors, in order to achieve its expression inside the eukaryotic cell (i.e. heterologous expression). By way of example, the present invention comprises heterologous sequences derived from virus (SEQ ID NO: 1 and 2) which are transferred into eukarytic cells in order to improve the expression of protein G receptors. As used herein, this term describes sequences from the methionine as the first codon of the coding sequence of a viral GPCR to the last amino acid of the extracellular amino terminal end of said viral GPCR sequence before the transmembrane 1 region of the aforesaid viral GPCR. As used in the methods of the present invention this term also preferably means, for example, viral sequences or fragments of sequences, isolated from mammalian beta and gamma herpesviruses GPCRs.

Hematopoietic cells: They are cells derived from bone marrow stem cells and comprise all the blood cell types that include both the myeloid (monocytes and macrophages, neutrophils, basophils, eosinophils, erythrocytes, megakaryocytes/platelets and some dendritic cells) and lymphoid lineages (T-cells, B-cells, NK-cells, some dendritic cells). Conversely, cells which do not derive from bone marrow are known as non-hematopoietic cells.

Sensor: It is a type of transducer. Sensors that transduce a biological signal are called biosensors. All living organisms contain biological sensors with functions similar to those of the mechanical sensors. Most of these are specialized cells that are sensitive to: light, motion, temperature, magnetic fields, gravity, humidity, vibration, pressure, electrical fields, sound, and other physical aspects of the external environment; physical aspects of the internal environment, such as stretch, motion of the organism, and position of appendages (proprioception); an enormous array of environmental molecules, including toxins, nutrients, and pheromones; many aspects of the internal metabolic milieu, such as glucose level, oxygen level, or osmolality; and a varied range of internal signal molecules, such as hormones, neurotransmitters, and cytokines. Artificial sensors that mimic biological sensors by using a biological sensitive component are called biosensors.

Cell line with regulated exocytosis: It refers to cell lines generally engineered to express a granule stored reporter that is released into the culture media by a modulator of exocytosis like a cell surface receptor, such as a GPCR after an agonist ligand binding. As used herein, the terms "cell with regulated exocytosis," "professional secretory cell line," and "cell line with professional regulated exocytosis" may be used interchangeably. All of these terms also include their progeny. It is understood that all progeny may not be identical due to deliberate or inadvertent mutations.

Drug discovery: process by which drugs are discovered and/or designed. As used herein drug discovery comprises drug identification and modifications for affinity, side effects, bioavailability but also testing the effect of a drug previously launched to the market in a new therapeutic indication, a process also known as reprofiling.

Gene: as used herein, a gene is composed not only of coding sequences but can comprise adjacent DNA regions involved in control of the transcription of the coding sequences (e.g., promoters, enhancers) and introns.

"Stably introduced" or "stably transformed" or "stably transduced" or "stably transfected" or "stably electroporated": It refers to the fraction of cells with the desirable foreign DNA integrated into their genome. Depending upon the expression vector and transfection technique used, only a fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and puromycin. Nucleic acid encoding a selectable marker can be introduced into a host cell on the same vector as that encoding a detectable translation product or can be introduced on a separate vector. Cells stably transfected with the introduced nucleic acid can be identified by drug selection (e.g., cells that have incorporated the selectable marker gene will survive, while the other cells die).

Chimeric receptors: The are receptors based on an artificial receptor that combine parts of one receptor with parts of another receptor, protein fragments, tag sequences or any combination thereof, including both entire domains and portions thereof. In general, a chimeric protein or "fusion protein" is a polypeptide comprising at least one portion of the desired protein product fused to at least another peptide sequence or to another polypeptide.

Vector or plasmid vector or plasmid: The term "vector" refers to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs).

Expression vector: The term "expression vector" refers to any type of genetic construct comprising a nucleic acid coding for RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleotide sequences that serve other functions as well and are described below.

Promoter: It is a regulatory region of DNA located upstream of a gene, providing a control point for regulated gene transcription. It may contain genetic elements at which regulatory proteins and molecules may bind, such as RNA polymerase and other transcription factors, to initiate the specific transcription a nucleic acid sequence. The phrases "operatively positioned," "operatively linked," "under the control," and "under transcriptional control" mean that a promoter is in a correct functional location and/or orientation in relation to a nucleic acid sequence to control transcriptional initiation and/or expression of that sequence.

Signal peptide or a signal sequence: A signal peptide is a short (3-60 amino acids long) peptide chain that directs the post-translational transport of a protein. Signal peptides may also be called targeting signals, signal sequences, transit peptides, or localization signals. The amino acid sequences of signal peptides direct proteins (which are synthesized in the cytosol) to certain organelles such as the nucleus, mitochondrial matrix, endoplasmic reticulum, chloroplast, apoplast and peroxisome. Some signal peptides are cleaved from the protein by signal peptidase after the proteins are transported.

Sequence tag: It is a short sub-sequence of a cDNA sequence that may be used to identify gene transcripts, and are generally involved in gene discovery and gene sequence determination for example with antibodies when specific antibodies to the protein are not available or for protein purification. Examples of known peptide tag that could be used for cell surface detection and separation are c-myc tag, HA tag and FLAG sup.TM tag. In general any peptide tag for which is available a specific binding protein could be used for surface detection and or separation provided such specific binding protein is labeled either directly or indirectly with a fluorophore or for example with a bead for surface separation.

Selectable marker or selectable marker sequence or selectable marker gene: It is a gene introduced into a cell that confers a trait suitable for artificial selection. They are a type of reporter gene used in laboratory microbiology, molecular biology, and genetic engineering to indicate the success of a transfection or other procedure meant to introduce foreign DNA into a cell. Selectable markers are often antibiotic resistance genes; bacteria that have been subjected to a procedure to introduce foreign DNA are grown on a medium containing an antibiotic, and those bacterial colonies that can grow have successfully taken up and expressed the introduced genetic material.

Transformation or transfection: as used herein refers to the introduction of foreign DNA into cells (e.g. prokaryotic or eukaryotic cells). Transformation may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. In particular transfection into eukaryotic cells could be transient when a suitable antibiotic is not included into the cell culture media for selection of cells bearing a stable integration of DNA into the chromosomes. Plasmid vectors for stable selection must have a selectable marker that is expressed into cells that are to be selected with an antibiotic. Although transient transfection could be used in the methods of the present invention preferred cells are those made stable by antibiotic selection.

Improved expression of the receptor GPCR in the surface of cells: This term means in the context of present specification either that the expression of said receptors is increased qualitatively (more expression per cell) or quantitatively (more cells expressing). That concept hence also means or comprises the experimental fact that cells which did not express GPCR in their surface, begin to express it. By analogy, the term "over-expression" as regard of present description means the same, mutatis mutandi, than the term improved expression when referred to the qualitatively expression per cell.

Comprising: This term, all along present patent description, includes, specifically, the term "consisting", when referred, particularly, to biological sequences, as amino acid or nucleotide sequences. It is meant that the sequence may either comprise a fragment on which the invention, taken as biological activity or technical effect, mainly resides, optionally jointly to other sequence fragments or sequence parts; or simply, being restricted precisely to the fragment as such.

Therefore the first embodiment of the present invention refers to the use of a nucleic acid sequence encoding for a heterologous-viral GPCR derived sequence for improving the expression of the eukaryotic receptor GPCR in the surface of eukaryotic cells in vitro. In a preferred embodiment the eukaryotic receptor GPCR is over-expressed in eukaryotic cells in vitro. In a still preferred embodiment the nucleic acid sequence encoding for a heterologous-viral GPCR derived sequence is characterized by comprising a DNA sequence represented by SEQ ID NO: 1 or SEQ ID NO: 2 or a DNA sequence encoding for an amino acid sequence comprising SEQ ID NO: 8 or SEQ ID NO: 9.

The second embodiment of the present invention refers to an isolated nucleic acid sequence encoding for a heterologous-viral receptor GPCR derived sequence characterized by comprising an nucleic acid represented by SEQ ID NO: 1 or SEQ ID NO: 2 or by comprising a nucleic acid encoding for an amino acid sequence comprising SEQ ID NO: 8 or SEQ ID NO: 9.

The third embodiment of tetracycline inducible promoter the present invention refers to a nucleic acid sequence encoding for a G protein-coupled receptor (GPCR), said encoding nucleic acid sequence being characterized by further comprising at least a part of the nucleic acid sequence encoding for a heterologous-viral GPCR derived sequence. In a preferred embodiment the part of said sequence encoding for the heterologous-viral GPCR derived sequence is characterized by comprising SEQ ID NO: 1 or SEQ ID NO: 2 or by comprising a fragment encoding for an amino acid sequence comprising SEQ ID NO: 8 or SEQ ID NO: 9. In a still preferred embodiment said nucleic acid sequence further comprising a signal peptide for improving surface expression and/or a sequence tag for surface detection and/or separation of cells positively expressing the heterologous-viral GPCR sequence. In a still preferred embodiment the sequence further comprises a promoter which can be an inducible promoter preferably selected from: ecdysone inducible promoter, cumate inducible promoter and progesterone inducible promoter or a constitutive promoter preferably selected from the sequences: SEQ ID NO: 3, SEQ ID NO: 4, SEQ ID NO: 5 and SEQ ID NO: 6.

The fifth embodiment of the present invention refers to an expression vector, preferably a plasmid, comprising the above described nucleic acid sequence. In a preferred embodiment the expression vector comprises the SEQ ID NO: 7.

The sixth embodiment of the present invention refers to non-human cells transfected with the above cited nucleic acid sequences or with said plasmid or expression vector. In a preferred embodiment the cells are eukaryotic cells preferably hematopoietic cells.

The seventh embodiment of the present invention refers to the use of the abover mentioned cells for screening the activity or influence of candidate compounds on the eukaryotic receptor GPCR.

The eighth embodiment of the present invention refers to a GPCR characterized by comprising at least a heterologous-viral GPCR derived sequence. In a preferred the heterologous-viral GPCR derived sequence is selected from those comprising an amino acid sequence represented by SEQ ID NO: 8 or SEQ ID NO: 9 or from those comprising an amino acid sequence encoded by a nucleic acid sequence comprising SEQ ID NO: 1 or SEQ ID NO: 2.

The ninth embodiment of the present invention refers to a GPCR which comprises an amino acid sequence encoded by the above mentioned nucleic acid sequences.

The tenth embodiment of the present invention refers to the use of said GPCR for screening the activity or influence of candidate compounds on the eukaryotic receptor GPCR.

The eleventh embodiment of the present invention refers to a cell membrane fraction enriched with said GPCR.

The twelfth embodiment of the present invention refers to the use of said membrane fraction for screening the activity or influence of candidate compounds on the eukaryotic receptor GPCR.

The thirteenth embodiment of the present invention refers to the a kit for testing the interaction of a candidate compound with an eukaryotic receptor GPCR that comprises a cell line according to the above described cells, or said cell membrane fraction enriched in GPCR, or the abovementioned GPCR and a substrate for determination of eukaryotic receptor GPCR activity. In a preferred embodiment the substrate is a fluorescent substrate for measuring intracellular calcium rise, a substrate of aequorin or a substrate for measuring cell regulated exocytosis.

The fourteenth embodiment of the present invention refers to an in vitro method for testing the interaction of a candidate compound with a eukaryotic receptor GPCR that comprises the addition of the candidate compound to a culture media along with a cell line according to the above mentioned cells, or with said membrane fraction enriched in GPCR, or the above mentioned GPCR and the determination of the eukaryotic receptor GPCR activity. In a preferred embodiment the determination of the eukaryotic receptor GPCR activity is carried out by means of a substrate, preferably a fluorescent substrate for measuring intracellular calcium rise, a substrate of aequorin or a substrate for measuring cell regulated exocytosis.

EXAMPLES

Example 1

Figure 1:
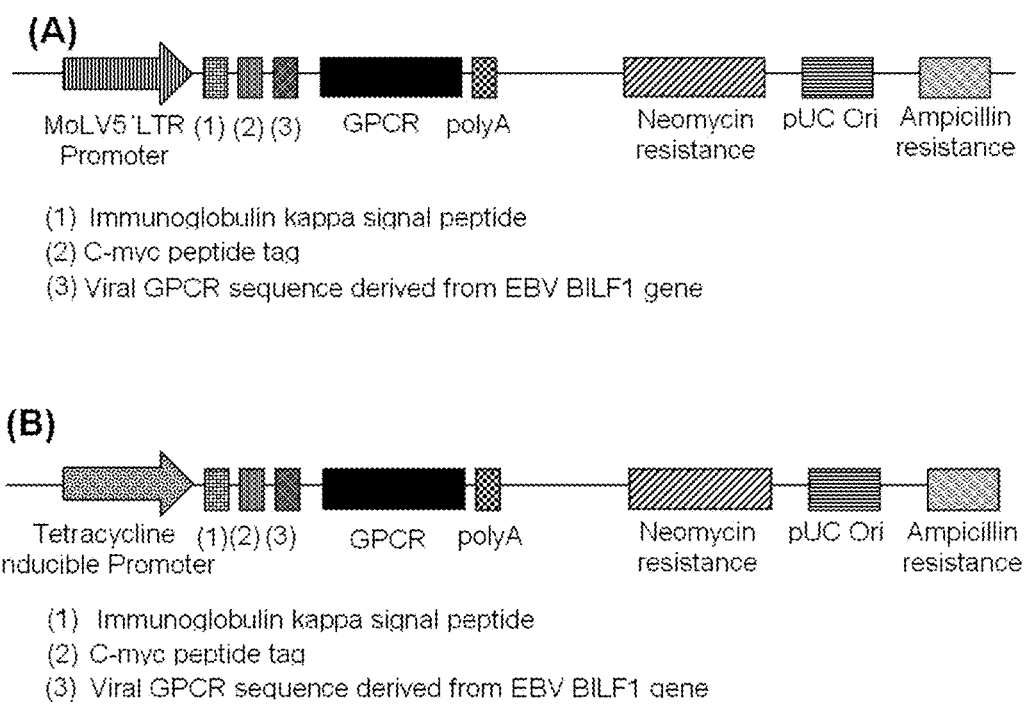
FIG. 1. Map of the plasmid vector with neomycin resistance used to express a functional surface receptor, such as a GPCR, using the signal peptide of mouse immunoglobulin kappa chain, a c-myc tag for surface detection with anti-cmyc monoclonal antibody and a viral-GPCR derived sequence for overexpression under the control of MoMLV5'LTR promoter (A) or under the control of Tetracycline Inducible Promoter (B).

Influence of Combinations of Promoters, Signal Peptide and Heterologous Viral-GPCR Sequence for Surface Expression of GPCRs in Hematopoietic Cells Vectors were developed for stable expression of GPCRs in hematopoietic cells with professional regulated exocytosis under the control of the following promoters: Moloney Leukaemia virus 5'-LTR (MoMLV5'LTR, SEQ ID NO: 6), human phosphoglycerate kinase promoter (SEQ ID NO: 4) and human elongation factor 1 alpha promoter (hEF1alpha, SEQ ID NO: 3). All vectors had the neomycin resistance gene for selection of stable eukaryotic cells, mouse immunoglobulin kappa signal peptide followed by a c-myc tag (EQKLISEEDLN peptide SEQ ID NO: 10) and the entire GPCR without the methionine at position 1. Each vector was individually electroporated using a microporator (Digital Bio Technology, South Korea) into RBL-2H3 and after 48 hours neomycin at 500 ug/mL was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Based on surface expression GPCRs were classified into three categories: GPCRs that were positive with all promoters tested with human interleukin-8 receptor as prototype; GPCRs that were positive with at least one of the promoters tested with human bradykinin type B1 receptor as prototype (was positive only with Moloney Leukaemia virus 5'-LTR promoter) and GPCRs that were negative with all promoters tested with human HTR1B receptor as prototype. Thus, new vectors were developed with human HTR1B receptor as a prototype of a receptor that is difficult to be expressed into hematopoietic cells like RBL-2H3. Vectors were developed for stable expression of human HTR1B in RBL-2H3 cells with professional regulated exocytosis under the control of the following promoters: Moloney Leukaemia virus 5'-LTR (MoMLV5'LTR, SEQ ID NO: 6), human phosphoglycerate kinase promoter (SEQ ID NO: 4) and human elongation factor 1 alpha promoter (hEF1alpha, SEQ ID NO: 3). All vectors had the neomycin resistance gene for selection of stable eukaryotic cells, mouse immunoglobulin kappa signal peptide followed by a c-myc tag (EQKLISEEDLN peptide), a sequence derived from a viral-GPCR sequence (VGS, SEQ ID NO: 2) and the entire human HTR1B without the methionine at position 1. Such heterologous viral-GPCR derived sequence was included to test if surface expression is improved by certain heterologous viral-GPCR derived sequences. Each vector was individually electroporated using a microporator (Digital Bio Technology, South Korea) into RBL-2H3 and after 48 hours neomycin at 500 ug/mL was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Results were expressed as percentage of positive cells after subtraction of values from non transfected RBL-2H3 cells incubated with the same anti-cmyc tag antibody. A percentage of less than 2 percent was indicated as such and was considered negative as isolation of such positive cells by MACS was unsuccessful. For positive cells mean fluorescence intensity (MFI) was taken as a marker of surface receptor density on the surface of positive cells. Results are shown in the following Table 1:

TABLE 1

| Promoter | Viral GPCR derived sequence (VGS) in vector (yes or no) | Percentage of positive cells after selection | Mean fluorescence intensity of positive cells (MFI) |
| --- | --- | --- | --- |
| hPGK promoter | No VGS | <2 | — |
| hPGK promoter | Yes | 5.6 | 49.2 |
| hEF1alpha promoter | No VGS | <2 | — |

TABLE 1-continued

| Promoter | Viral GPCR derived sequence (VGS) in vector (yes or no) | Percentage of positive cells after selection | Mean fluorescence intensity of positive cells (MFI) |
| --- | --- | --- | --- |
| hEF1alpha promoter | Yes | 10 | 56.9 |
| MoMLV5'LTR promoter | No VGS | <2 | — |
| MoMLV5'LTR promoter | Yes | 13.7 | 40.3 |
| RSV promoter | No VGS | 5 | 29.3 |
| RSV promoter | Yes | 5.6 | 82.4 |

Thus for HTR1B the inclusion of a heterologous viral-GPCR derived sequence in the vector to increase surface expression was positive with all promoters tested. Curiously, for a new promoter tested for expression of HTR1B the inclusion of a heterologous viral-GPCR derived sequence does not improved the percentage of positive cells but the MFI of positive cells was increased 2.8 fold. When vectors were developed for new GPCR including the VGS and either hEF1alpha promoter or MoMLV-5'LTR promoter and stably transfected vectors with VGS performed always equal or better than their VGS negative counterparts. Such GPCR tested to date included: BDKRB1, AGTR1, CX3CR1, GRM4, AVPR2, DRD1, DRD2, EDNRB, TACR3, ADORA3, HTR1B, CHRM2, IL8RA, NPY1R, ADRA2A, ADRAB2, CCKBR, SSTR2, MC1R, BB2R and CHHR1. The same results were also true in other hematopoietic cells like 32D and P815 cells and results shown for HTR1B in RBL-2H3 are representative of the effect of a heterologous viral-GPCR derived sequence on surface expression of all tested GPCRs in several hematopoietic cells lines. Thus, the above results indicate that the addition of a heterologous viral-GPCR derived sequence to a GPCR improves surface expression and is thus useful for the methods of the present invention.

Example 2

Influence of Heterologous Viral-GPCR Derived Sequence for Surface Expression of GPCRs in Other Eukaryotic Cells Vectors were developed for stable expression of GPCRs in hematopoietic cells without professional regulated exocytosis under the control of Moloney Leukaemia virus 5'-LTR (MoMLV5'LTR, SEQ ID NO: 6), a good promoter for expression of GPCRs tested previously for more than 20 different GPCRs. The vector had neomycin resistance gene for selection of stable eukaryotic cells, mouse immunoglobulin kappa signal peptide followed by a c-myc tag (EQKLISEEDLN peptide) and the entire HT1BR GPCR without the methionine at position 1. This GPCR is a prototype of a receptor that it is difficult to be expressed into RBL-2H3. Two vectors were developed: one with a heterologous viral-GPCR derived sequence (VGS) and one without VGS. Each vector was individually electroporated using a microporator (Digital Bio Technology, South Korea) into WEHI-3B, a mouse myelomonocytic leukaemia cell line (DSMZ, ACC26) and into BW5147.G.1.4.ovar.1, a mouse lymphoma T cell line (HPA cultures, Cat. No. 88100507) and after 48 hours neomycin was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Results are shown in the following Table 2:

TABLE 2

| Promoter | Viral GPCR derived sequence (VGS) in vector (yes or no) | Percentage of positive cells after selection | Mean fluorescence intensity of positive cells (MFI) |
|---|---|---|---|
| WEHI 3B CELLS | | | |
| MoMLV5'LTR promoter | No VGS | 30.58 | 16.92 |
| MoMLV5'LTR promoter | Yes | 50.24 | 18.81 |
| BW5147 CELLS | | | |
| MoMLV5'LTR promoter | No VGS | 2.70 | 20.90 |
| MoMLV5'LTR promoter | Yes | 39.6 | 17.13 |

Thus, the inclusion of a heterologous viral-GPCR derived sequence in the vector increases surface expression of HT1BR in both WEHI-3B cells and BW5147 cells. While in the first cell line the improvement is from about 30% to about 50% for a ratio of 1.6 times, the effect in BW5147 cells is about 15 times higher percentage of cells with surface expression. Thus, VGS is a sequence that when added to the amino terminus of GPCRs improve their surface expression in hematopoietic cell lines without professional exocytosis.

Example 3

Influence of Heterologous Viral-GPCR Derived Sequence on the Surface Expression of GPCRs in Non-Hematopoietic Cells Vectors were developed for stable expression of GPCRs in mammalian cells under the control of the following promoters: Moloney Leukaemia virus 5'-LTR (MoMLV5'LTR, SEQ ID NO: 6), human phosphoglycerate kinase promoter (SEQ ID NO: 4) and human elongation factor 1 alpha promoter (hEF1alpha, SEQ ID NO: 3). All vectors had the neomycin resistance gene for selection of stable eukaryotic cells, mouse immunoglobulin kappa signal peptide followed by a c-myc tag (EQKLISEEDLN peptide), a sequence derived from a heterologous viral-GPCR (VGS, SEQ ID NO: 2) and the entire human HTR1B without the methionine at position 1. Such heterologous viral-GPCR derived sequence was included to test if surface expression is improved by certain heterologous viral-GPCR derived sequences in non-hematopoietic cell lines. Each vector was individually electroporated using a microporator (Digital Bio Technology, South Korea) into HEK293 cells (DSMZ, ACC305) and after 48 hours neomycin at 1000 ug/mL was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Results were expressed as percentage of positive cells after subtraction of values from non transfected HEK293 cells incubated with the same anti-cmyc tag antibody. A percentage of less than 2 percent was indicated as such and was considered negative as isolation of such positive cells by MACS was unsuccessful. For positive cells mean fluorescence intensity (MFI) was taken as a marker of surface receptor density on the surface of positive cells. Results are shown in the following Table 3:

TABLE 3

| Promoter | Viral GPCR derived sequence (VGS) in vector (yes or no) | Percentage of positive cells after selection | Mean fluorescence intensity of positive cells (MFI) |
|---|---|---|---|
| hPGK promoter | No VGS | 6.88 | 28.36 |
| hPGK promoter | Yes | 14.48 | 38.96 |
| hEF1alpha promoter | No VGS | 11.48 | 29.85 |
| hEF1alpha promoter | Yes | 17.52 | 46.51 |
| MoMLV5'LTR promoter | No VGS | 5.76 | 32.79 |
| MoMLV5'LTR promoter | Yes | 15.48 | 38.66 |
| RSV promoter | No VGS | <2 | — |
| RSV promoter | Yes | 3.74 | 29.16 |

Thus for HTR1B stably transfected into HEK293, a widely used non-hematopoietic cell line of human embryonic kidney, the inclusion of a heterologous viral-GPCR derived sequence in the vector increases surface expression for all promoters tested. The MoMLV5'LTR that is a good promoter for expression of GPCRs into hematopoietic cell lines is also a good promoter for HEK293 and the inclusion of a VGS improves 2.7 fold the percentage of positive cells. This example demonstrates that heterologous viral-GPCRs derived sequences are useful for surface expression of GPCRs in heterologous cells and this improvement is not limited to hematopoietic cells, but also to other eukaryotic cells.

Example 4

Influence of Mutations of VGS on the Surface Expression of GPCRs

Vectors were developed for stable expression of human HTR1B without the methionine at position 1 in mammalian cells under the control of Moloney Leukaemia virus 5'-LTR promoter (MoMLV5'LTR, SEQ ID NO: 6). All vectors had the neomycin resistance gene for selection of stable eukaryotic cells and mouse immunoglobulin kappa signal peptide followed by a c-myc tag (EQKLISEEDLN peptide). Vectors included no VGS, native VGS or two VGS mutants (VGS mutant 1 and VGS mutant 2). This experiment was designed to test if serine and threonine at VGS which represent potential N-linked glycosylation sites are the molecular determinants of improved surface expression. In VGS mutant 1 all 5 serine and threonine were mutated to alanine while in VGS mutant 2 all serine were mutated and 2 threonines were still present.

Sequences of different VGS used in this experiment are the following:

```
Native short VGS (LSTMAPGSTVGT, SEQ ID NO: 9).

VGS mutant 1 (LAAMAPGAAVGA, SEQ ID NO: 11).

VGS mutant 2 (LAAMAPGATVGT, SEQ ID NO: 12).
```

Each vector was individually electroporated by triplicate using a microporator (Digital Bio Technology, South Korea) into RBL-2H3 and after 48 hours neomycin at 500 ug/mL was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Selected cells were separated by using magnetic beads from Miltenyi and anti-cmyc tag. Results were expressed as percentage of positive cells after subtraction of values from non transfected RBL-2H3 cells incubated with the same anti-cmyc tag antibody. For positive cells median fluorescence intensity (x-median) was taken as a marker of surface receptor density on the surface of positive cells. Results are shown in the following Table 4:

TABLE 4

| VGS type used for expression | Percentage of positive cells after selection (range) | Median fluorescence intensity of positive cells, x-median (range) |
| --- | --- | --- |
| No VGS | 41.0 (39.8-42.1) | 33.8 (33.3-34.3) |
| VGS native | 50.2 (49.2-51.1) | 89.3 (87.7-90.9) |
| VGS mutant 1 | 49.1 (47.5-50.7) | 45.6 (44.9-46.2) |
| VGS mutant 2 | 49.2 (48.2-50.2) | 62.4 (60.6-64.2) |

The above results indicate that the inclusion of native VGS improves cell surface expression as both percentage of positive cells increased from 41% to 50% but also the median of fluorescence intensity of positive cells increased from 33.8 to 89.3, that is, increased 2.6 fold. In addition the above results indicate that mutation of serine and threonine predicted in silico to be O-glycosylated (VGS mutant 2) reduced median fluorescence intensity from 89.3 to 62.4 that is reduced median 1.43 fold but there was no variation in the percentage of positive cells by such mutation, while mutation of all serine and threonine of VGS including those that are not predicted to be glycosylated, reduced median fluorescence intensity from 89.3 to 45.6 that, is about 2 fold, but again did not change percentage of positive cells. The above results demonstrate that the effect of viral derived GPCR sequences on surface expression of GPCRs is in part but not fully due to serines and threonines. If such serines and threonines are glycosylated is not known at present but if so, then other properties than potential O-glycosylation also explain why VGS improve cell surface expression of GPCRs.

The invention claimed is:

1. A chimeric GPCR comprising an eukaryotic GPCR and at least one amino acid sequence selected from the group consisting of SEQ ID NO: 9, SEQ ID NO: 12, SEQ ID NO: 13, and the amino acid sequence encoded by the nucleic acid sequence set forth in SEQ ID NO: 2, wherein the at least one amino acid sequence is added at the N-terminal end of the eukaryotic GPCR, and wherein the chimeric GPCR improves the expression of the eukaryotic GPCR on the cell surface.

2. A cell membrane fraction comprising a chimeric GPCR according to claim 1.

3. A kit for testing the interaction of a candidate compound with an eukaryotic receptor GPCR, said kit comprising a cell membrane fraction according to claim 2 and a substrate for determination of an eukaryotic receptor GPCR activity.

4. A kit for testing the interaction of a candidate compound with an eukaryotic receptor GPCR, said kit comprising a chimeric GPCR according to claim 1 and a substrate for determination of an eukaryotic receptor GPCR activity selected from fluorescent substrate for measuring intracellular calcium rise, a substrate of aequorin or a substrate for measuring cell regulated exocytosis.

5. A method of improving the expression of a eukaryotic receptor GPCR on the surface of eukaryotic cells in vitro, said method comprising transfecting a nucleic acid sequence that encodes a chimeric GPCR according to claim 1 into eukaryotic cells.

6. The method, according to claim 5, wherein the eukaryotic receptor GPCR is over-expressed in eukaryotic cells in vitro.

* * * * *